(12) United States Patent
Mesiwala

(10) Patent No.: US 10,448,977 B1
(45) Date of Patent: Oct. 22, 2019

(54) INTERSPINOUS DEVICE AND RELATED METHODS

(71) Applicant: Ali H. Mesiwala, Claremont, CA (US)

(72) Inventor: Ali H. Mesiwala, Claremont, CA (US)

( * ) Notice: Subject to any disclaimer, the term of this patent is extended or adjusted under 35 U.S.C. 154(b) by 0 days.

(21) Appl. No.: 13/854,938

(22) Filed: Apr. 1, 2013

Related U.S. Application Data

(60) Provisional application No. 61/618,690, filed on Mar. 31, 2012.

(51) Int. Cl.
*A61B 17/70* (2006.01)

(52) U.S. Cl.
CPC ................. *A61B 17/7062* (2013.01)

(58) Field of Classification Search
CPC . A61B 17/7068; A61B 17/7067; A61B 17/60; A61B 17/68; A61B 17/70; A61B 17/7001; A61B 17/701; A61B 17/7011; A61B 17/7047; A61B 17/7049; A61B 17/705; A61B 17/7062
USPC .......................................... 606/246–249, 279
See application file for complete search history.

(56) References Cited

U.S. PATENT DOCUMENTS

| | | |
|---|---|---|
| 267,269 A | 11/1882 | Smith et al. |
| 2,677,369 A | 5/1954 | Knowles |
| 3,025,853 A | 3/1962 | Mason |
| 3,242,922 A | 3/1966 | Thomas |
| 3,426,364 A | 2/1969 | Lumb |
| 3,648,691 A | 3/1972 | Lumb et al. |
| 3,805,219 A | 4/1974 | Bright |
| 4,143,883 A | 3/1979 | Paynter |
| 4,448,191 A | 5/1984 | Rodnyansky et al. |
| 4,554,914 A | 11/1985 | Kapp et al. |
| 4,570,618 A | 2/1986 | Wu |
| 4,604,995 A | 8/1986 | Stephens et al. |
| 4,611,582 A * | 9/1986 | Duff ............................. 606/258 |
| 4,643,178 A | 2/1987 | Nastari et al. |
| 4,655,462 A | 4/1987 | Balsells |
| 4,773,402 A | 9/1988 | Asher et al. |
| 4,913,134 A | 4/1990 | Luque |
| 5,011,484 A | 4/1991 | Breard |
| 5,084,049 A | 1/1992 | Asher et al. |
| 5,092,866 A | 3/1992 | Breard et al. |
| 5,167,662 A | 12/1992 | Hayes et al. |
| 5,180,393 A | 1/1993 | Commarmond |
| 5,261,914 A | 11/1993 | Warren |
| 5,304,178 A | 4/1994 | Stahurski |
| 5,352,225 A | 10/1994 | Yuan et al. |
| 5,437,672 A * | 8/1995 | Alleyne ................. A61B 17/00 606/279 |
| 5,458,641 A * | 10/1995 | Ramirez Jimenez ...... 623/17.11 |
| 5,470,333 A | 11/1995 | Ray |

(Continued)

FOREIGN PATENT DOCUMENTS

| | | |
|---|---|---|
| DE | 3114872 | 10/1982 |
| EP | 1872731 | 1/2008 |

(Continued)

*Primary Examiner* — Ellen C Hammond
*Assistant Examiner* — Tessa M Matthews

(57) ABSTRACT

The present invention involves a device and method for restoring intervertebral height and promoting bone fusion to maintain the proper height. The present invention is an interspinous device comprised of two clamps and an elongated element for use in spinal surgery to separate adjacent vertebrae. Once deposited in the intervertebral space, the device effects spinal fusion over time as the natural healing process fuses the bone through and around the device.

15 Claims, 2 Drawing Sheets

(56) References Cited

U.S. PATENT DOCUMENTS

| | | | |
|---|---|---|---|
| 5,496,318 A | 3/1996 | Howland et al. | |
| 5,531,747 A | 7/1996 | Ray | |
| 5,609,634 A | 3/1997 | Voydeville | |
| 5,645,599 A | 7/1997 | Samani | |
| 5,722,976 A | 3/1998 | Brown | |
| 5,836,948 A | 11/1998 | Zucherman et al. | |
| 6,048,342 A | 4/2000 | Zucherman et al. | |
| 6,312,431 B1 | 11/2001 | Asfora | |
| 6,364,883 B1 | 4/2002 | Santilli | |
| 6,582,433 B2 | 6/2003 | Yun | |
| 6,626,944 B1 | 9/2003 | Taylor | |
| 6,641,585 B2 | 11/2003 | Sato et al. | |
| 6,652,527 B2 | 11/2003 | Zucherman et al. | |
| 6,652,534 B2 | 11/2003 | Zucherman et al. | |
| 6,695,842 B2 | 2/2004 | Zucherman et al. | |
| 6,699,246 B2 | 3/2004 | Zucherman et al. | |
| 6,699,247 B2 | 3/2004 | Zucherman et al. | |
| 6,712,819 B2 | 3/2004 | Zucherman et al. | |
| 6,761,720 B1 | 7/2004 | Senegas | |
| 6,796,983 B1 | 9/2004 | Zucherman et al. | |
| 7,048,736 B2 | 5/2006 | Robinson et al. | |
| 7,201,775 B2 | 4/2007 | Gorensek et al. | |
| 7,252,673 B2 | 8/2007 | Lim | |
| 7,306,628 B2 | 12/2007 | Zucherman et al. | |
| 7,361,179 B2 | 4/2008 | Rousseau et al. | |
| 7,520,888 B2 | 4/2009 | Trieu | |
| 7,588,592 B2 | 9/2009 | Winslow et al. | |
| 7,727,233 B2 | 6/2010 | Blackwell et al. | |
| 7,758,274 B2 | 7/2010 | Paul | |
| 7,776,069 B2 | 8/2010 | Taylor | |
| 7,828,847 B2 | 11/2010 | Abdou | |
| 7,837,688 B2 | 11/2010 | Boyer, II et al. | |
| 7,842,074 B2 | 11/2010 | Abdou | |
| 7,993,374 B2* | 8/2011 | Zucherman et al. | 606/249 |
| 8,048,120 B1 | 11/2011 | Fallin et al. | |
| 8,128,659 B2 | 3/2012 | Ginsberg et al. | |
| 8,172,882 B2* | 5/2012 | Klyce et al. | 606/276 |
| 8,241,330 B2 | 8/2012 | Lamborne et al. | |
| 8,267,697 B2 | 9/2012 | Kirschman | |
| 8,343,190 B1 | 1/2013 | Mueller et al. | |
| 8,357,181 B2* | 1/2013 | Lange et al. | 606/248 |
| 8,382,801 B2 | 2/2013 | Lamborne et al. | |
| 8,790,373 B2* | 7/2014 | Aflatoon | 606/249 |
| 10,076,366 B2* | 9/2018 | Wang | A61B 17/7055 |
| 2001/0021850 A1 | 9/2001 | Zucherman et al. | |
| 2003/0040746 A1 | 2/2003 | Mitchell et al. | |
| 2003/0065330 A1 | 4/2003 | Zucherman et al. | |
| 2003/0094812 A1 | 5/2003 | Balsells | |
| 2003/0216736 A1 | 11/2003 | Robinson et al. | |
| 2003/0236472 A1 | 12/2003 | Van Hoeck et al. | |
| 2004/0260291 A1 | 12/2004 | Jensen | |
| 2005/0033434 A1 | 2/2005 | Berry | |
| 2005/0165398 A1 | 7/2005 | Reiley | |
| 2005/0203624 A1* | 9/2005 | Serhan et al. | 623/17.11 |
| 2006/0036256 A1 | 2/2006 | Carl et al. | |
| 2006/0036258 A1 | 2/2006 | Zucherman et al. | |
| 2006/0064095 A1 | 3/2006 | Senn et al. | |
| 2006/0084987 A1* | 4/2006 | Kim | A61B 17/70 606/258 |
| 2006/0106381 A1 | 5/2006 | Ferree et al. | |
| 2006/0106397 A1 | 5/2006 | Lins | |
| 2006/0136060 A1 | 6/2006 | Taylor | |
| 2006/0235532 A1 | 10/2006 | Meunier et al. | |
| 2006/0241601 A1 | 10/2006 | Trautwein et al. | |
| 2006/0247633 A1 | 11/2006 | Winslow et al. | |
| 2006/0247640 A1 | 11/2006 | Blackwell et al. | |
| 2006/0293662 A1 | 12/2006 | Boyer, II et al. | |
| 2007/0093823 A1 | 4/2007 | Booth et al. | |
| 2007/0093825 A1 | 4/2007 | Ferree et al. | |
| 2007/0093828 A1 | 4/2007 | Abdou | |
| 2007/0100340 A1* | 5/2007 | Lange | A61B 17/7065 606/279 |
| 2007/0173832 A1 | 7/2007 | Tebbe et al. | |
| 2007/0191948 A1* | 8/2007 | Arnin | A61B 17/7043 623/17.11 |
| 2007/0225724 A1 | 9/2007 | Edmond | |
| 2007/0233074 A1 | 10/2007 | Anderson et al. | |
| 2007/0233077 A1 | 10/2007 | Khalili | |
| 2007/0233088 A1 | 10/2007 | Edmond | |
| 2007/0233096 A1 | 10/2007 | Garcia-Bengochea | |
| 2007/0233129 A1 | 10/2007 | Bertagnoli et al. | |
| 2007/0270812 A1 | 11/2007 | Peckham | |
| 2007/0270824 A1 | 11/2007 | Lim et al. | |
| 2007/0270827 A1 | 11/2007 | Lim et al. | |
| 2007/0270874 A1 | 11/2007 | Anderson | |
| 2007/0276370 A1 | 11/2007 | Altarac et al. | |
| 2007/0299445 A1 | 12/2007 | Shadduck et al. | |
| 2008/0027438 A1 | 1/2008 | Abdou | |
| 2008/0033552 A1 | 2/2008 | Lee et al. | |
| 2008/0039837 A1 | 2/2008 | Gambale | |
| 2008/0051896 A1 | 2/2008 | Suddaby | |
| 2008/0114401 A1 | 5/2008 | Liu et al. | |
| 2008/0114455 A1 | 5/2008 | Lange et al. | |
| 2008/0140125 A1 | 6/2008 | Mitchell et al. | |
| 2008/0161818 A1 | 7/2008 | Kloss et al. | |
| 2008/0167655 A1 | 7/2008 | Wang et al. | |
| 2008/0177271 A1 | 7/2008 | Yeh | |
| 2008/0177298 A1 | 7/2008 | Zucherman et al. | |
| 2008/0177391 A1 | 7/2008 | Mitchell et al. | |
| 2008/0228225 A1* | 9/2008 | Trautwein et al. | 606/246 |
| 2008/0234735 A1 | 9/2008 | Joshi | |
| 2008/0269904 A1 | 10/2008 | Voorhies | |
| 2008/0281359 A1 | 11/2008 | Abdou | |
| 2008/0294199 A1 | 11/2008 | Kohm et al. | |
| 2008/0300686 A1 | 12/2008 | Khoo | |
| 2008/0312741 A1 | 12/2008 | Lee et al. | |
| 2009/0054931 A1 | 2/2009 | Metz-Stavenhagen | |
| 2009/0062915 A1 | 3/2009 | Kohm et al. | |
| 2009/0062918 A1 | 3/2009 | Wang et al. | |
| 2009/0082808 A1 | 3/2009 | Butler et al. | |
| 2009/0105773 A1 | 4/2009 | Lange et al. | |
| 2009/0198277 A1 | 8/2009 | Gordon et al. | |
| 2009/0204151 A1 | 8/2009 | Bracken | |
| 2009/0264275 A1 | 10/2009 | Ginsberg et al. | |
| 2009/0326581 A1 | 12/2009 | Galley et al. | |
| 2010/0069965 A1 | 3/2010 | Abdou | |
| 2010/0087860 A1 | 4/2010 | Chin et al. | |
| 2010/0087869 A1 | 4/2010 | Abdou | |
| 2010/0121381 A1* | 5/2010 | Berta | A61B 17/7055 606/264 |
| 2010/0211101 A1 | 8/2010 | Blackwell et al. | |
| 2010/0211102 A1 | 8/2010 | Belliard et al. | |
| 2010/0318128 A1 | 12/2010 | Abdou | |
| 2011/0004248 A1 | 1/2011 | Abdou | |
| 2011/0022090 A1 | 1/2011 | Gordon et al. | |
| 2011/0029020 A1* | 2/2011 | Gordon | A61B 17/7062 606/248 |
| 2011/0054531 A1 | 3/2011 | Lamborne et al. | |
| 2011/0066186 A1 | 3/2011 | Boyer, II et al. | |
| 2011/0087286 A1* | 4/2011 | Ciupik et al. | 606/249 |
| 2011/0144692 A1 | 6/2011 | Saladin et al. | |
| 2011/0271653 A1* | 11/2011 | Vandeven | A01D 41/141 56/10.2 E |
| 2011/0319936 A1 | 12/2011 | Gordon et al. | |
| 2012/0016418 A1 | 1/2012 | Chin et al. | |
| 2012/0016419 A1 | 1/2012 | Aflatoon | |
| 2012/0065682 A1 | 3/2012 | Duong et al. | |
| 2012/0089184 A1 | 4/2012 | Yeh | |
| 2012/0101528 A1 | 4/2012 | Souza et al. | |
| 2012/0109198 A1 | 5/2012 | Dryer et al. | |
| 2012/0109203 A1 | 5/2012 | Dryer et al. | |
| 2012/0109205 A1 | 5/2012 | Mitchell et al. | |
| 2012/0136390 A1 | 5/2012 | Butler et al. | |
| 2012/0150228 A1 | 6/2012 | Zappacosta et al. | |
| 2012/0191135 A1 | 7/2012 | Abdou | |
| 2012/0215261 A1 | 8/2012 | Massoudi | |
| 2012/0221050 A1 | 8/2012 | Ingalhalikar et al. | |
| 2012/0226312 A1* | 9/2012 | Thalgott et al. | 606/246 |
| 2012/0226314 A1 | 9/2012 | Chin et al. | |
| 2012/0245641 A1 | 9/2012 | Mekhail et al. | |
| 2012/0290008 A1 | 11/2012 | Kirschman | |
| 2012/0310282 A1 | 12/2012 | Abdou | |
| 2013/0012996 A1 | 1/2013 | Samani et al. | |
| 2013/0030467 A1 | 1/2013 | Karas et al. | |

(56) References Cited

U.S. PATENT DOCUMENTS

| | | |
|---|---|---|
| 2013/0060284 A1 | 3/2013 | Abdou |
| 2013/0072979 A1 | 3/2013 | Butler et al. |
| 2013/0103086 A1 | 4/2013 | Marik et al. |
| 2013/0158604 A1 | 6/2013 | Okamoto |
| 2013/0184751 A1 | 7/2013 | Siegfried |
| 2013/0184752 A1 | 7/2013 | Binder |
| 2013/0184754 A1 | 7/2013 | Taber et al. |
| 2013/0190820 A1 | 7/2013 | Siegfried et al. |
| 2013/0197581 A1 | 8/2013 | Justis et al. |
| 2013/0204301 A1 | 8/2013 | Mitchell et al. |
| 2014/0228885 A1* | 8/2014 | Dinville et al. ............. 606/249 |
| 2015/0335363 A1* | 11/2015 | Walsh .................. A61B 17/707 606/249 |

FOREIGN PATENT DOCUMENTS

| | | |
|---|---|---|
| FR | 1037262 | 9/1953 |
| FR | 2703239 | 10/1994 |
| FR | 2806614 | 9/2001 |
| FR | 2902639 | 12/2007 |
| FR | 2930718 | 11/2009 |
| GB | 780652 | 8/1957 |
| WO | WO 1993/014721 | 8/1993 |
| WO | WO 1994/020048 | 9/1994 |
| WO | WO 2003/007829 | 1/2003 |
| WO | WO 2003/024298 | 3/2003 |
| WO | WO 2004/039283 | 5/2004 |
| WO | WO 2006/086241 | 8/2006 |
| WO | WO 2006/110578 | 10/2006 |
| WO | WO 2007/038475 | 4/2007 |
| WO | WO 2007/087535 | 8/2007 |
| WO | WO 2007/089975 | 8/2007 |
| WO | WO 2007/106573 | 9/2007 |
| WO | WO 2008/067452 | 6/2008 |
| WO | WO 2008/106140 | 9/2008 |
| WO | WO 2009/135208 | 11/2009 |
| WO | WO 2009/152126 | 12/2009 |

\* cited by examiner

INTERSPINOUS DEVICE AND RELATED METHODS

CROSS REFERENCE TO RELATED APPLICATIONS

This application claims the benefit of the filing date of U.S. Provisional Patent Application No. 61/618,690 which was filed on Mar. 31, 2012. The contents of U.S. Application No. 61/618,690 is incorporated by reference as part of this application.

FIELD OF THE INVENTION

The present invention relates generally to spinal surgery and, in particular, to methods and an apparatus for providing space to and supporting adjacent interspinous processes.

BACKGROUND

With age, individuals' spinal discs and vertebral facets may degenerate, which can result in a decrease in the disc space height. This degeneration can cause a reduction in the size of the foramen of the vertebrae. The foramen is a natural opening between the vertebrae that allows the passage of respective nerves from the spinal cord. With degeneration of the spinal discs or vertebral facets, the nerves may become compressed by the reduced foramen space leading to various types of back pain.

To restore the intervertebral height and relieve the pain, a number of interspinous process devices have been designed. Intervertebral spinal inserts are used to provide support and maintain normal distance between adjacent vertebrae in cases where a patient's vertebral discs have degenerated. Intervertebral inserts are typically used to reestablish normal intervertebral spacing and to cause fusion between adjacent vertebral bodies.

SUMMARY

The present invention is an interspinous device dimensioned for implantation between two adjacent vertebral bodies to restore intervertebral height and maintain distraction of the spinous processes.

According to one broad aspect of the present invention, the device comprises two clamps, one at the superior end and the other at the inferior end, and an elongated component connecting between the two clamps.

A clamp may include any number of components capable of securing the spinous process or lamina. By way of example only, each clamp may be designed in a generally U shaped configuration allowing a vertebral body to fit within the U shape. According to one embodiment, the interior surface of the clamp has anti-migration features. The clamps will provide a compressive force against the bone to ensure the implant doesn't migrate once in place, providing stabilization for proper bone fusion.

The superior and inferior clamps are separated by and coupled to an elongated component capable of maintaining the distance between the clamps. By way of example only, an elongated component may include a bar, a trough or a cage. This component can vary in length as necessary for the specific patient needs. The component is dimensioned to be filled with bone fusion promoting materials.

Two clamps and an elongated component are designed such that the construct may be assembled at the time of surgery. Various sized elongated components may be used interchangeably with the clamps, so that this element can be chosen at the time of surgery providing the flexibility for surgeons to account for needed distraction height.

The clamps are attached to the base of the spinous process or lamina, one on the inferior portion of the superior vertebrae and the other on the superior portion of the inferior vertebrae. The affected vertebral space is distracted with a ratcheting distractor utilizing the clamps of the current invention. When decompression has been achieved and the desired height restored, an elongated component of appropriate size is placed between the clamps to maintain the intervertebral height. The elongated component is slid into position and locked into place connecting to each of the clamps. Bone fusion is facilitated through the elongated component, stabilizing the vertebrae and providing lasting restorative height to the vertebral space.

BRIEF DESCRIPTION OF THE DRAWINGS

Many advantages of the present invention will be apparent to those skilled in the art with a reading of this specification in conjunction with the attached drawings, wherein like reference numerals are applied to like elements and wherein.

DETAILED DESCRIPTION

Illustrative embodiments of the invention are described below. In the interest of clarity, not all features of an actual implementation are described in this specification. It will of course be appreciated that in the development of any such actual embodiment, numerous implementation-specific decisions must be made to achieve the developers' specific goals, such as compliance with system-related and business-related constraints, which will vary from one implementation to another. Moreover, it will be appreciated that such a development effort might be complex and time-consuming, but would nevertheless be a routine undertaking for those of ordinary skill in the art having the benefit of this disclosure. The interspinous device disclosed herein boasts a variety of inventive features and components that warrant patent protection, both individually and in combination.

Figure 1:
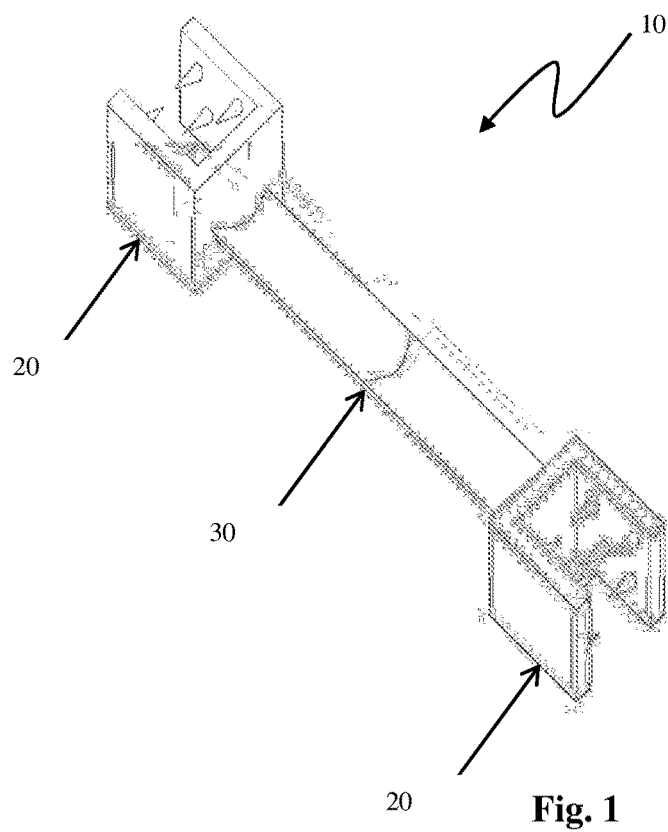
FIG. 1 is a perspective view of an assembled interspinous device, comprising one clamp at the distal end and one clamp at the proximal end, connected by a trough.
Figure 2:
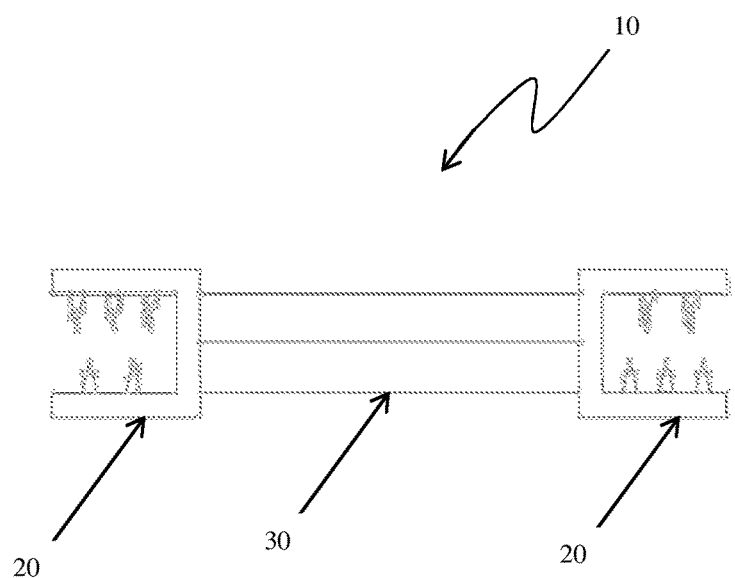
FIG. 2 is a lateral view of the assembled invention of FIG. 1.
Figure 3:
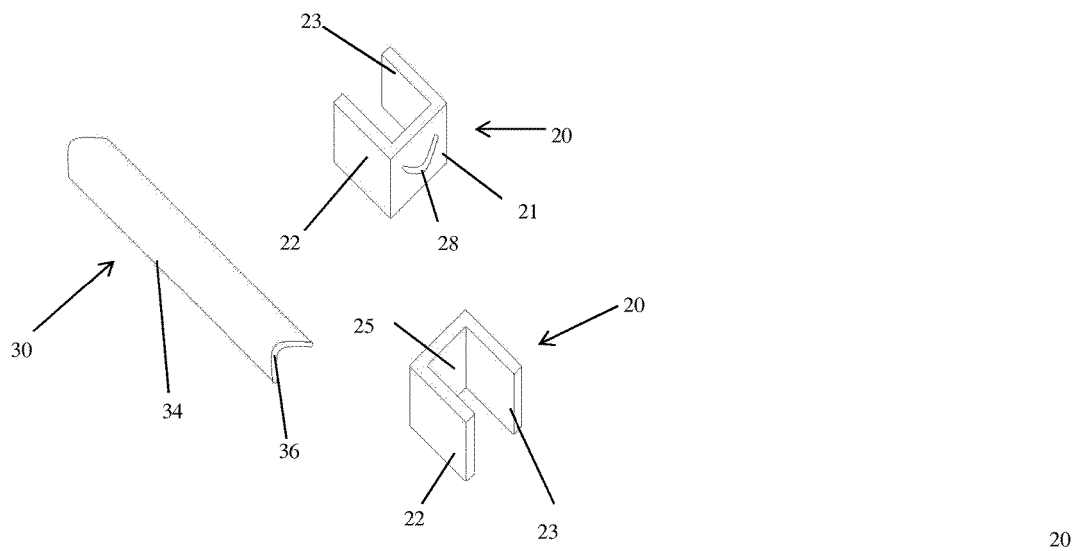
FIG. 3 is an exploded view of the invention of FIG. 1.
Figure 4:
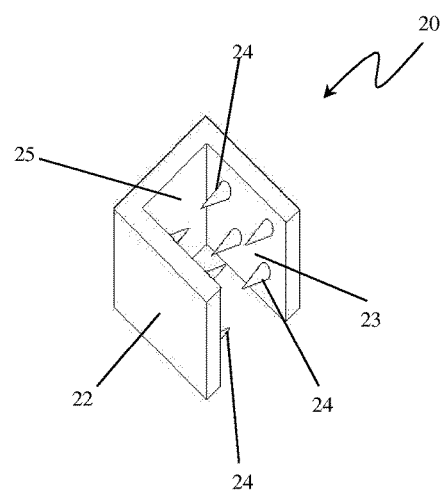
FIG. 4 is a perspective view of the clamp of FIG. 1.

FIGS. 1-2 illustrate the interspinous device 10. The interspinous device 10 includes a clamp 20 at the superior end and another clamp 20 at the inferior end. The interspinous device 10 also includes an elongated member 30 that connecting the two clamps 20.

As seen in FIGS. 1-4, the clamps are generally U-shaped, defined by two lateral walls 22 and transverse wall 21. The clamps are such that they grasp the lamina or spinous process of a given vertebra, providing a compressive force between the arms of the clamp to ensure stability and fixation. The interior surfaces 23 of the lateral walls 22 may be equipped with any number of anti-migration features. In one embodiment, the interior surfaces 23 will have a number of teeth 24 to engage the spinous process or lamina when implanted. The interior surface 25 of the inferior wall 21 may also include anti-migration features, such as ridges or teeth. The exterior surface of the transverse wall 21 has an engagement mechanism 28 for connecting to the elongated member 30. For example, the engagement mechanism can be a female feature 28 to receive a male engagement feature 36 on the elongated member 30. The engagement mechanism may also be a male feature to connect to a female feature of the elongated member 30.

Figure 5:
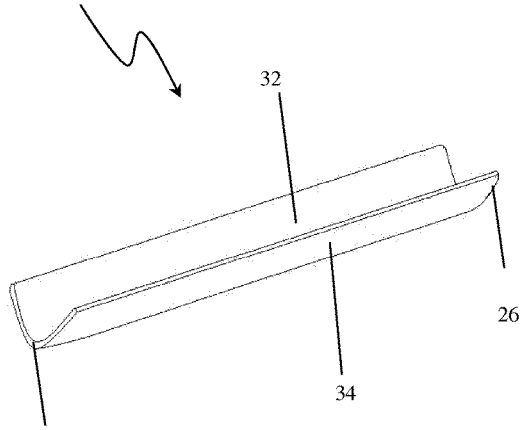
FIG. 5 is a perspective view of the trough of FIG. 1.

An elongated component connects the two clamps, providing support and restoring and maintaining intervertebral height. The elongated component may be any number of elements that are capable of achieving this purpose, including an elongated bar, a trough, or a cage. As illustrated in FIG. 5, in an exemplary embodiment, the elongated component is a trough 30 with a convex shape, comprised of an outer surface 34, an inner surface 32, and a proximal end 26 and distal end 27. The outer, convex surface 34 is smooth and implanted facing the spinal canal to shield the delicate anatomy contained therein. The inner, concave surface 32 is shaped to receive and hold bone fusion promoting materials. The superior and inferior ends comprise an engagement mechanism or may be shaped for connecting to an engagement mechanism on the exterior of the transverse wall 21 of each of the clamps. The elongated component is designed in a variety of lengths to provide the correct distraction height for the given surgical needs.

The interspinous device 10 is a three piece design, with two clamps 20 and a trough 30. The pieces are designed such that they can be easily connected at the time of surgery. The method for the surgical technique involved with this interspinous device includes: (1) the placement of the clamps on the base of the spinous process or lamina of the affected adjacent vertebrae, (2) the use of a ratcheting distractor with the clamps, (3) distracting the interspinous space in discrete increments, such as, for example, 2 mm increments, (3) decompressing the affected interspinous space, (4) selecting the appropriate elongated element size based on a distractor gauge, (5) sliding the elongated element into position and locking it to clamps, and (6) inducing arthrodesis through the elongated element.

While the invention is susceptible to various modifications and alternative forms, specific embodiments thereof have been shown by way of example in the drawings and are herein described in detail. It should be understood, however, that the description herein of specific embodiments is not intended to limit the invention to the particular forms disclosed, but on the contrary, the invention is to cover all modifications, equivalents, and alternatives falling within the spirit and scope of the invention as defined herein.

What is claimed is:

1. A spinal implant for implantation between a superior spinous process and an inferior spinous process, comprising:
   a first U-shaped clamp having two lateral walls, a transverse wall, and an open end opposite the transverse wall, the clamp adapted to firmly grasp the superior spinous process in between the transverse and lateral walls and maintain the superior spinous process therein by interaction with a plurality of anti-migration features positioned on an interior surface of the lateral walls;
   a second clamp configured to be coupled to the inferior spinous process; and
   an elongated trough configured to provide support to the clamps and restore and maintain an intervertebral height between the processes, the elongated trough coupled to each of the first clamp and the second clamp, the elongated trough having a convex anterior surface and a concave posterior surface, such that the elongated trough has a constant U-shaped transverse cross-section along its entire longitudinal axis extending between the first clamp and the second clamp, and which two U-shaped ends couple directly with each of the transverse wall of the first clamp and the second clamp, respectively,
   wherein the first clamp, second clamp, and elongated trough are each a separate modular component configured to be implanted independently of each other.

2. The spinal implant of claim 1, wherein the elongated trough is of unitary construction.

3. The spinal implant of claim 1, wherein the elongated trough has a proximal end and a distal end, wherein the first clamp is coupled to the elongated trough at the proximal end and the second clamp is coupled to the elongated trough at the distal end.

4. The spinal implant of claim 1, wherein the second clamp is generally U-shaped.

5. The spinal implant of claim 4, wherein the second clamp has an open end oriented in a direction opposite the open end of the first clamp.

6. The spinal implant of claim 1, wherein the anti-migration features are spikes.

7. The spinal implant of claim 1, wherein the second clamp has at least one bone-facing surface and wherein the bone-facing surface includes anti-migration features.

8. The spinal implant of claim 7, wherein the anti-migration features of the second clamp are spikes.

9. The spinal implant of claim 1, wherein the convex anterior surface of the elongated trough is smooth.

10. The spinal implant of claim 1, wherein the elongated trough is dimensioned to receive graft material therein.

11. The spinal implant of claim 1, wherein the first clamp has a U-shaped slot to receive one of the U-shaped ends of the elongated trough.

12. The spinal implant of claim 11, wherein the second clamp has a U-shaped slot to receive the other U-shaped end of the elongated trough.

13. The spinal implant of claim 1, wherein the two lateral walls each extend from the transverse wall along an axis parallel to the longitudinal axis of the trough.

14. A spinal implant for implantation between a superior spinous process and an inferior spinous process, comprising:
   a first U-shaped clamp having two lateral walls each having an interior surface, a transverse wall, and an open end opposite the transverse wall, and a plurality of spikes disposed on each of the interior surfaces of the two lateral walls;
   a second clamp configured to be coupled to the inferior spinous process; and
   an elongated trough configured to provide support to the clamps and restore and maintain an intervertebral height between the processes, the elongated trough coupled to each of the first clamp and the second clamp, the elongated trough having a convex anterior surface and a concave posterior surface, such that the elongated trough has a constant U-shaped transverse cross-section along its entire longitudinal axis extending between the first clamp and the second clamp, and which two U-shaped ends couple directly with each of the transverse wall of the first clamp and the second clamp, respectively, wherein the first clamp, second clamp, and elongated trough are each a separate modular component configured to be implanted independently of each other.

15. A spinal implant for implantation between a superior spinous process and an inferior spinous process, comprising:
   a first U-shaped clamp having two lateral walls, a transverse wall, and an open end opposite the transverse wall, the clamp adapted to firmly grasp the superior spinous process in between the transverse and lateral walls and maintain the superior spinous process therein by interaction with a plurality of anti-migration features positioned on an interior surface of the lateral walls;

a second clamp configured to be coupled to the inferior spinous process; and an elongated trough configured to provide support to the clamps and restore and maintain an intervertebral height between the processes, the elongated trough coupled to each of the first clamp and the second clamp, the elongated trough having a convex anterior surface and a concave posterior surface, such that the elongated trough has a constant U-shaped transverse cross-section along its entire longitudinal axis extending between the first clamp and the second clamp, and which two U-shaped ends couple directly with each of the transverse wall of the first clamp and the second clamp, respectively, wherein the first clamp has a U-shaped slot to receive one of the U-shaped ends of the elongated trough.

\* \* \* \* \*